(12) United States Patent
Nishida et al.

(10) Patent No.: US 8,933,404 B2
(45) Date of Patent: Jan. 13, 2015

(54) CONCENTRATION MEASUREMENT METHOD AND CONCENTRATION MEASUREMENT APPARATUS

(75) Inventors: Kazuhiro Nishida, Nagano (JP); Kazuhiko Amano, Tokyo (JP); Koichi Shimizu, Hokkaido (JP)

(73) Assignees: Seiko Epson Corporation, Tokyo (JP); National University Corporation Hokkaido University, Hokkaido (JP)

( * ) Notice: Subject to any disclaimer, the term of this patent is extended or adjusted under 35 U.S.C. 154(b) by 499 days.

(21) Appl. No.: 13/425,537

(22) Filed: Mar. 21, 2012

(65) Prior Publication Data

US 2012/0242979 A1    Sep. 27, 2012

(30) Foreign Application Priority Data

Mar. 23, 2011    (JP) ................. 2011-064627

(51) Int. Cl.
  *G01N 21/17* (2006.01)
  *A61B 5/145* (2006.01)
  *A61B 5/1455* (2006.01)

(52) U.S. Cl.
  CPC .... *A61B 5/14532* (2013.01); *G01N 2021/1734* (2013.01); *A61B 5/1455* (2013.01)
  USPC ............. 250/339.07; 250/339.08; 250/339.09

(58) Field of Classification Search
  CPC ..................... G01N 21/17; G01N 21/1734
  USPC ....................... 250/339.07–339.09
  See application file for complete search history.

(56) References Cited

U.S. PATENT DOCUMENTS

| 6,195,574 | B1 * | 2/2001 | Kumar et al. ................. 600/323 |
| 2008/0287809 | A1 | 11/2008 | Amano et al. |
| 2010/0256920 | A1 * | 10/2010 | Amano et al. .................. 702/23 |
| 2013/0073220 | A1 * | 3/2013 | Nishida et al. .................. 702/25 |

FOREIGN PATENT DOCUMENTS

| JP | 52-063397 A | 5/1977 |
| JP | 2003-050200 A | 2/2003 |
| JP | 2007-050162 A | 3/2007 |
| JP | 3903147 B | 4/2007 |
| JP | 2007-259967 A | 10/2007 |
| JP | 2008-264518 A | 11/2008 |
| JP | 2010-237139 A | 10/2010 |

* cited by examiner

*Primary Examiner* — Casey Bryant
(74) *Attorney, Agent, or Firm* — Global IP Counselors, LLP (57) ABSTRACT

A concentration measurement method by an absorptiometric method which measures a concentration of a first solute component dissolved in a solution, in which the first solute component interacts with a solvent, includes: referring to an absorption coefficient ($\mu_{aw}(\lambda)$) of the solvent; measuring an absorption coefficient ($\mu_a(\lambda)$) of a first sample material, after an interaction between the solvent and the first solute component has occurred; and obtaining an unknown volume fraction ($v_g$) of the first solute component and a volume fraction ($v_w$) of the solvent, based on the absorption coefficient ($\mu_{aw}(\lambda)$) of the solvent, a apparent absorption coefficient ($\mu'_{ag}(\lambda)$) of the first solute component, and the absorption coefficient ($\mu_a(\lambda)$) of the first sample material.

12 Claims, 8 Drawing Sheets

ABSORBANCE COEFFICIENT OR APPARENT ABSORBANCE COEFFICIENT OF EACH COMPONENTS

FIG. 7

$\mu_{ag}(\lambda)$ :
 ABSORPTION COEFFICIENT OF
 GLUCOSE SOLVATED BY WATER (mm$^{-1}$)
$\mu_{aw}(\lambda)$ :
 ABSORPTION COEFFICIENT OF WATER (BULK WATER)
 NOT BOUND WITH GLUCOSE(mm$^{-1}$)
$\mu_{aw2}(\lambda)$ : ABSORPTION COEFFICIENT OF WATER
 (HYDRATED WATER) BOUND WITH GLUCOSE(mm$^{-1}$)
$v_g$ : VOLUME FRACTION OF GLUCOSE
$v_w$ : VOLUME FRACTION OF WATER($=v_{w1}+v_{w2}$)
$v_{w1}$ : VOLUME FRACTION OF BULK WATER
$v_{w2}$ : VOLUME FRACTION OF HYDRATED WATER

FIG. 10

CONCENTRATION MEASUREMENT METHOD AND CONCENTRATION MEASUREMENT APPARATUS

CROSS-REFERENCE TO RELATED APPLICATION

This application claims priority on Japanese Patent Application No. 2011-064627, filed Mar. 23, 2011, the contents of which are incorporated herein by reference.

BACKGROUND

1. Technical Field

The present invention relates to a concentration measurement apparatus and a concentration measurement method that quantitates a concentration of target component among an observation target composed of a plurality of layers of light scattering medium, in a non-invasive manner and with an excellent accuracy.

2. Related Art

In recent years, Japan is said to be in the era of satiation, with yearly increasing number of diabetes patients. The number of diabetic nephropathy is also increasing, resulting in an yearly increase of ten thousand patients of chronic renal failure, with a total patient number of over 280 thousand.

On the other hand, under increasing demand of preventive medicine in the advent of the aging society, the importance of the personal metabolic rate control is drastically rising. In particular, it has been known that by blood sugar level measurements before and after meals, the sugar metabolism reaction can be evaluated. Evaluation of the sugar metabolism reaction in the very early stage of diabetes enables an early treatment of diabetes based on early stage diagnosis.

In the past, blood sugar level measurement has been done by taking blood samples from veins in the arm or the finger tip, and measuring enzymatic activity to the glucose in the blood sample. However, there have been various problems in that such blood sugar level measurement requires tedious and painful blood drawing and also involves risk of infectious disease.

Moreover, as a method to continuously measure blood sugar level, devices have been developed in the united states, that continuously perform glucose quantitation corresponding to the blood sugar level while an injection needle is kept inserted. Such devices are currently under clinical trials. However, keeping the injection needle inserted in the vein causes risks of unintended removal of the needle during the blood sugar level measurement, and also risks of infectious diseases.

Under these circumstances, demands has been growing for a development of blood sugar level measurement apparatus that can measure blood sugar level frequently without blood drawing, and is free of infectious disease risks. Demands also has been growing for a development of blood sugar level measurement apparatus that is easily and continuously wearable, and capable of being downsized.

As apparatus that non-invasively measures component concentrations, proposed devices adopt regular absorptiometric principals and use the methods of molecular absorbance measurement.

Such apparatus irradiates light with a specific wavelength or continuous wavelength on the measurement subject, measures the light absorbance, and calculates the component concentration based on the Beer-Lambert law.

However, apparatus that calculates glucose concentration based on the Beer-Lambert law has a problem in that under circumstances where the subject components interact with each other, e.g., cluster formation, in which the Beer-Lambert law is not applicable, a precise measurement can not be performed. For example, when the glucose level in the blood is measured, because of the influence of the interaction between glucose and water (liquid) in the blood, and the interaction between water and salt in the blood, precise measurements of concentration of such components are difficult.

On the other hand, some apparatus acts without relying on the Beer-Lambert law, in which a calibration curve is prepared in advance using subject materials with known concentrations, and then a sample material with unknown concentration is subject to absorbance measurement, and the absorbance is compared with the calibration curve to obtain the concentration of the subject sample material (see, e.g., JP-A-52-63397 and JP-B-3903147).

However, such measurement apparatus using the calibration curve, has a problem in that when an unexpected component other than the subject component is included, the variation in concentration of the unexpected component causes a change in the absorption by the subject component, resulting in a considerable measurement errors.

Some other apparatus using the calibration curve takes into account this concentration variation of components other than the subject component, and utilize a multivariate analysis (see, e.g., JP-A-2003-050200 and JP-A-2007-259967).

In such measurement apparatus (measurement methods) using the multivariate analysis, the calibration curve is prepared using a simulative method, in which the interaction between the components are not considered. In cases including multiple subject components, those components interact with each other. As the interaction between the components becomes larger, the measurement error of the concentration also becomes larger, causing difficulties in accurate measurements of the subject components.

It is conceivable to prepare a calibration curve by, instead of simulations, actually measuring multiple samples. However, such calibration curve preparation in consideration of mutual interactions is not practical because it excessively consumes time and work.

SUMMARY

According to an advantage of some aspects of the invention, a concentration measurement method and a concentration measurement apparatus may be provided, in which concentrations of solute components which interact with the solvent can be accurately quantitated based on the Beer-Lambert law, even when components other than the measurement subject exists.

An aspect of the invention provides a concentration measurement method by an absorptiometric method which measures a concentration of a first solute component dissolved in a solution, in which the first solute component interacts with a solvent, including: referring to an absorption coefficient ($\mu_{aw}(\lambda)$) of the solvent; referring to an apparent absorption coefficient ($\mu'_{ag}(\lambda)$) of the first solute component, which is measured in advance, after an interaction between the solvent and the first solute component has occurred; measuring an absorption coefficient ($\mu_a(\lambda)$) of a first sample material, after the interaction between the solvent and the first solute component has occurred; and obtaining an unknown volume fraction ($v_g$) of the first solute component and a volume fraction ($v_w$) of the solvent, based on the absorption coefficient ($\mu_{aw}(\lambda)$) of the solvent, the apparent absorption coefficient ($\mu'_{ag}(\lambda)$) of the first solute component, and the absorption coefficient ($\mu_a(\lambda)$) of the first sample material, by solving a system of instances of Equation 1 applied to two different wavelengths, or by solving a system of Equation 1 applied to one wavelength and Equation 2.

$$\mu_a(\lambda) = \mu'_{ag}(\lambda) \cdot v_g + \mu_{aw}(\lambda) \cdot v_w \quad \text{(Equation 1)}$$

$$v_g + v_w = 1 \quad \text{(Equation 2)}$$

Another aspect of invention provides, in a case in which the solution further includes a second solute component, a concentration measurement method by an absorptiometric method which measures a concentration of a solute component dissolved in a solution, in which the solute component interacts with a solvent, including: referring to an absorption coefficient ($\mu_{aw}(\lambda)$) of the solvent; referring to an apparent absorption coefficient ($\mu'_{ag}(\lambda)$) of a first solute component, which is measured in advance, after an interaction between the solvent and the first solute component has occurred; referring to an apparent absorption coefficient ($\mu'_{an}(\lambda)$) of a second solute component, which is measured in advance, after an interaction between the solvent and the second solute component has occurred; measuring an absorption coefficient ($\mu_a(\lambda)$) of a first sample material, after the interaction between the solvent and the first solute component and the interaction between the solvent and the second solute component have occurred; obtaining a volume fraction ($v_g$) of the first solute component, a volume fraction ($v_n$) of the second solute component, and a volume fraction ($v_w$) of the solvent, based on the absorption coefficient ($\mu_{aw}(\lambda)$) of the solvent, the apparent absorption coefficient ($\mu'_{ag}(\lambda)$) of the first solute component, the apparent absorption coefficient ($\mu'_{an}(\lambda)$) of the second solute component, and the absorption coefficient ($\mu_a(\lambda)$) of the first sample material, by solving a system of instances of Equation 3 applied to three different wavelengths, or by solving a system of instances of Equation 3 applied to two different wavelengths and Equation 4.

$$\mu_a(\lambda) = \mu'_{ag}(\lambda) \cdot v_g + \mu'_{an}(\lambda) \cdot v_n + \mu_n + \mu_{aw} \cdot v_w \quad \text{(Equation 3)}$$

$$v_g + v_n + v_w = 1. \quad \text{(Equation 4)}$$

It may be configured in the measuring an absorption coefficient ($\mu_a(\lambda)$) of the first sample material, a light source wavelength of the absorptiometric method is set so that the apparent absorption coefficient ($\mu'_{ag}(\lambda)$) of the first solute component or the apparent absorption coefficient ($\mu'_{an}(\lambda)$) of the second solute component becomes a negative value.

It may be configured the light source wavelength is in the range of 1370 nm to 1510 nm, or in the range of 1550 nm to 1740 nm.

It may be configured the light source wavelength is in the range of 1370 nm to 1420 nm.

Another aspect of the invention provides a concentration measurement apparatus that measures a concentration of a first solute component in a solution, in which the first solute component interacts with a solvent, the concentration measurement apparatus including: a memory that stores an absorption coefficient ($\mu_{aw}(\lambda)$) of the solvent, an apparent absorption coefficient ($\mu'_{ag}(\lambda)$) of the first solute component measured in advance after an interaction occurred between the solvent and the first solute component; a measurement part that measures an absorption coefficient ($\mu_a(\lambda)$) of a first sample material in which a concentration of the first solute component is unknown, after the interaction between the solvent and the first solute component has occurred; a light source that irradiates a light of a predetermined wavelength at the first sample material; and a calculator that calculates a volume fraction ($v_g$) of the first solute component and a volume fraction of the solvent ($v_w$), based on the absorption coefficient ($\mu_{aw}(\lambda)$) of the solvent, the apparent absorption coefficient ($\mu'_{ag}(\lambda)$) of the first solute component, and the absorption coefficient ($\mu_a(\lambda)$) of the first sample material, by solving a system of instances of Equation 1 applied to two different wavelengths, or by solving a system of Equation 1 applied to one wavelength and Equation 2.

$$\mu_a(\lambda) = \mu'_{ag}(\lambda) \cdot v_g + \mu_{aw}(\lambda) \cdot v_w \quad \text{(Equation 1)}$$

$$v_g + v_w = 1 \quad \text{(Equation 2)}$$

Another aspect of the invention provides a concentration measurement apparatus that measures a concentration of a first solute component in a solution, in which the first solute component interacts with a solvent, the concentration measurement apparatus including: a memory that stores an absorption coefficient ($\mu_{aw}(\lambda)$) of the solvent, an apparent absorption coefficient ($\mu'_{ag}(\lambda)$) of the first solute component measured in advance after an interaction occurred between the solvent and the first solute component, and an apparent absorption coefficient ($\mu'_{an}(\lambda)$) of the second solute component measured in advance after an interaction occurred between the solvent and the second solute component; a measurement part that measures an absorption coefficient ($\mu_a(\lambda)$) of a first sample material in which a concentration of the first solute component and a concentration of the second solute component, after the interaction between the solvent and the first solute component and the interaction between the solvent and the second solute component have occurred, are unknown; a light source that irradiates a light of a predetermined wavelength at the first sample material; and a calculator that calculates a volume fraction ($v_n$) of the second solute component, and a volume fraction of the solvent ($v_w$), based on the absorption coefficient ($\mu_a w(\lambda)$) of the solvent, the apparent absorption coefficient ($\mu'_{ag}(\lambda)$) of the first solute component, the apparent absorption coefficient ($\mu'_{an}(\lambda)$) of the second solute component, and the absorption coefficient ($\mu_a(\lambda)$) of the first sample material, by solving a system of instances of Equation 3 applied to three different wavelengths, or by solving a system of instances of Equation 3 applied to two different wavelengths and Equation 4.

$$\mu_a(\lambda) = \mu'_{ag}(\lambda) \cdot v_g + \mu'_{an}(\lambda) \cdot v_n + \mu_{aw} \cdot v_w \quad \text{(Equation 3)}$$

$$v_g + v_n + v_w = 1 \quad \text{(Equation 4)}$$

It may be configured the light source irradiates a light having a wavelength so that the apparent absorption coefficient ($\mu'_{ag}(\lambda)$) of the first solute component or the apparent absorption coefficient ($\mu'_{an}(\lambda)$) of the second solute component becomes a negative value.

DESCRIPTION OF EXEMPLARY EMBODIMENTS

Hereinafter, concentration measurement apparatuses and concentration measurement methods according to exemplary embodiments of the invention will be explained. Here, a blood sugar level measurement apparatus as an example of concentration measurement apparatus, human palm skin as an example of observation target, and glucose as an example of target component will be shown.

First Embodiment

Figure 1:
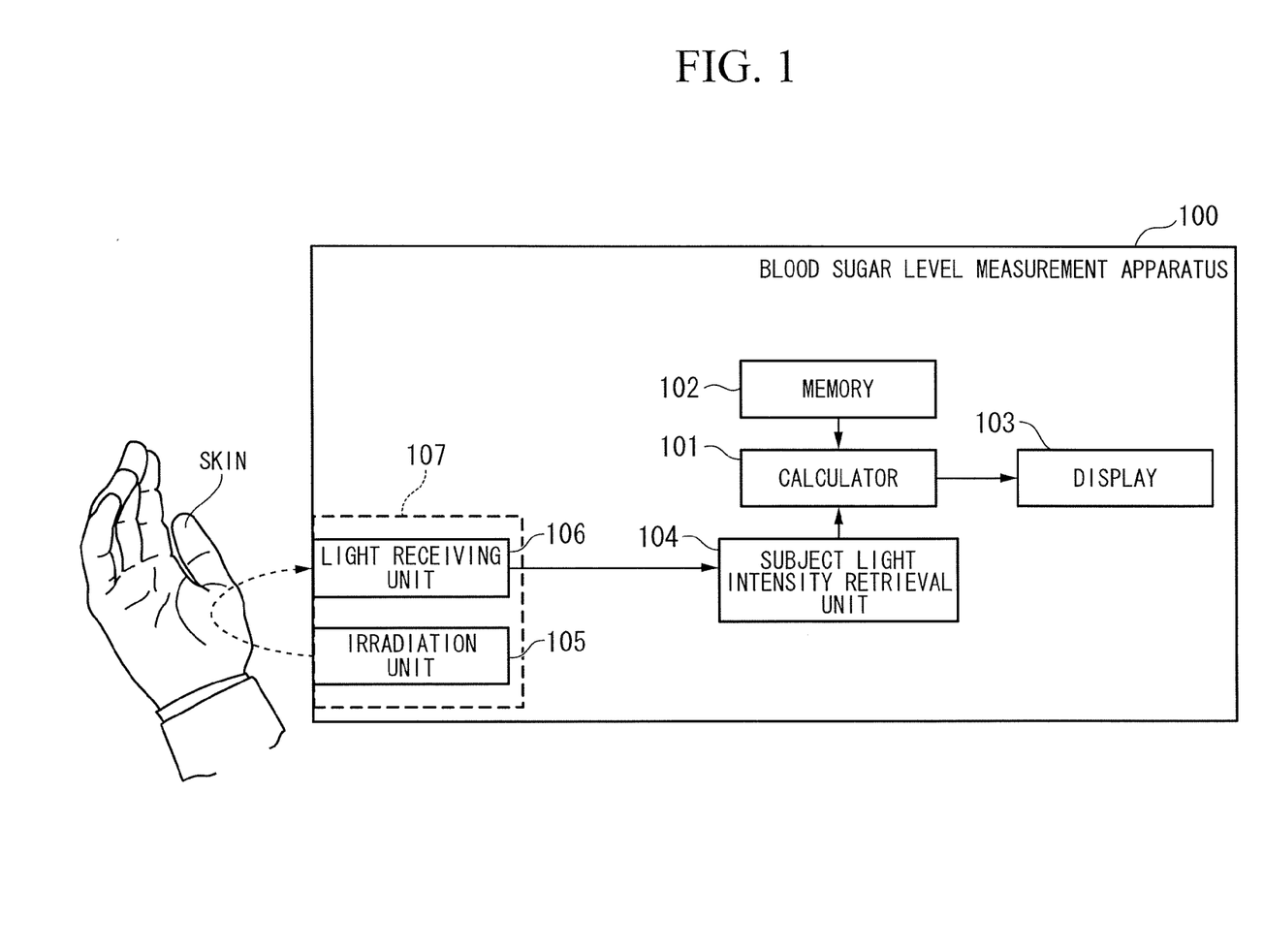
FIG. 1 is a schematic block diagram showing a blood sugar level measurement apparatus according to a first embodiment of the invention.

FIG. 1 is a schematic block diagram showing a constitution of blood sugar level measurement apparatus according to the first embodiment of the invention. Basic configurations and methods are similar to the first embodiment. The features specific to this embodiment will be explained below.

This blood sugar level measurement apparatus 100 can precisely measure the concentration of a first solute component dissolved in a solution in which the first solute component shows an interaction when dissolved in the solvent. The measurement is performed through an absorptiometric method. The apparatus includes a measurement unit 107 having a calculator 101, a memory 102, a display 103, a subject light intensity retrieval unit (measurement part) 104, an irradiation unit 105, and a light receiving unit 106 and a light receiving unit 106.

This blood sugar level measurement apparatus 100 measures, for example, measures (quantitates), for example, concentration of one of the components consisting body fluid (sample material; solution) that exists in dermic layer (or any other layer of interest) of skin, i.e., glucose (first solute component), as a first solute component, that is, a first solute component that is subjected to interactions when dissolved in water (solvent).

Here, the interaction includes effects from cluster formation that occurs when the solute is dissolved in the water, e.g., change in number of intermolecular hydrogen bonds, hydrogen bonds between water and the glucose in the glucose solution, and ionic bonds between water and sodium chloride.

The memory 102 stores absorption coefficient ($\mu_{aw}(\lambda)$) of the water (solvent), and apparent absorption coefficients ($\lambda_{ag}(\lambda)$) of glucose (first solute component) after glucose is dissolved in the water that is measured using glucose solutions having known concentrations.

A subject light intensity retrieval unit (measurement part) 104 measures the absorption coefficient ($\mu_a(\lambda)$) of a first sample material, i.e., body fluid that exists in dermic layer (or any other layer of interest) of skin, after the interaction of water and glucose has occurred, in which the glucose concentration is unknown.

The irradiation unit (light source) 105 irradiates light having a predetermined wavelength on the skin (observation target). This irradiation unit (light source) 105 may, for example, include laser light source. The irradiation unit 105 may have, for example, a light source which irradiate a wavelength so that the apparent absorption coefficient ($\mu'_{ag}(\lambda)$) of glucose (first solute component) becomes a negative value. The irradiation unit 105 further irradiates a pulse light for a short amount of time at the skin. This plurality of short time pulse light includes light of the wavelength which results in a higher orthogonality of the absorption spectra distribution of each of the main components constituting skin. That is, the wavelength of the included light is set so that, among the main components constituting skin, a particular component of interest have a maximum in the absorptive spectrum thereof that is significantly distant from the maximum of the absorption spectra of the other components.

Based on the absorption coefficient ($\mu_{aw}(\lambda)$) of the water (solvent), the known apparent absorption coefficient ($\mu'_{ag}(\lambda)$) of glucose, and an apparent absorption coefficient ($\mu_a(\lambda)$) of observation target having an unknown glucose concentration, the calculator 101 calculates, an unknown volume fraction ($v_g$) of glucose, and the volume fraction ($V_w$) of the solvent. Such calculator 101 may include, for example, a CPU and memories.

The light receiving unit 106 may receive, for example, the back scatter light from the skin of the short time pulse light.

Here, the structure of human skin tissues as the observation target will be explained.

Figure 2:
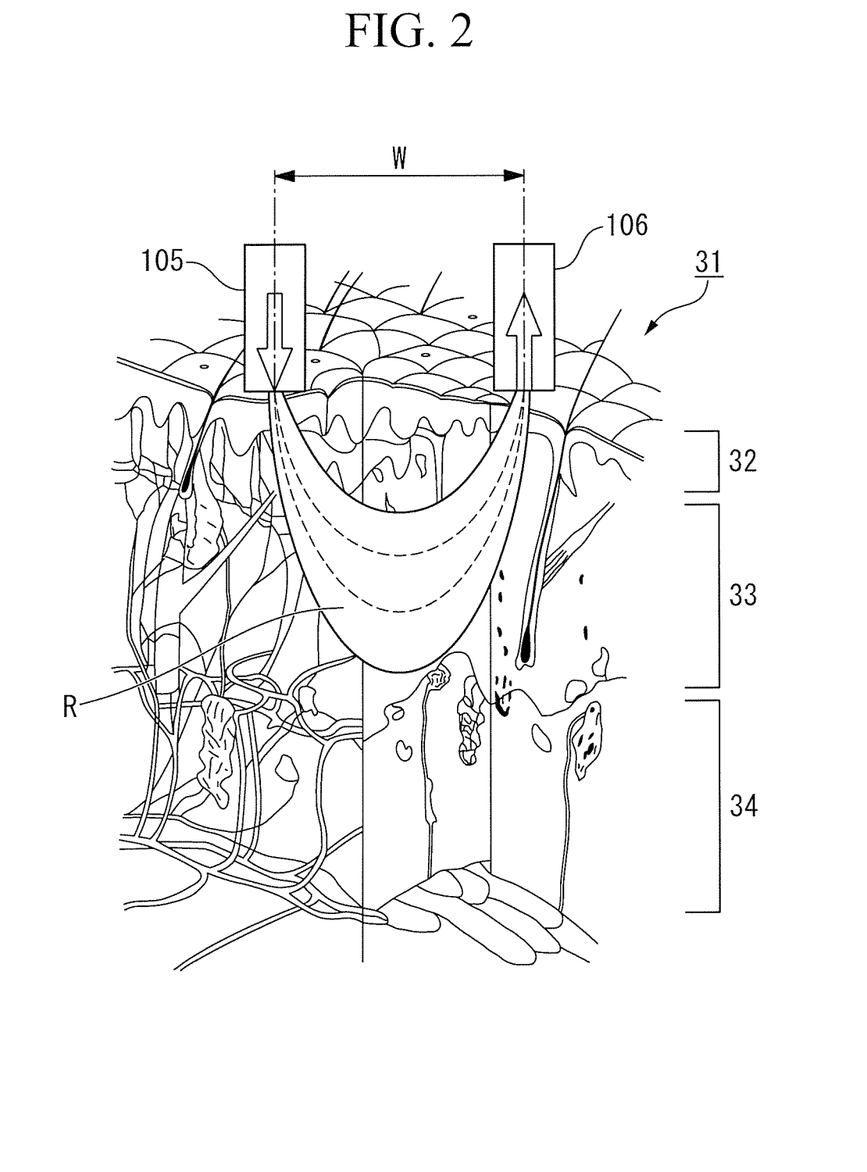
FIG. 2 is a schematic view of an intersection of human skin tissue.

FIG. 2 is a schematic view of an intersection of human skin tissue. Skin 31 is constituted with three layers, i.e., an epidermis layer 32, a dermic layer (any layer) 33, and hypodermis 34.

The epidermis layer 32 is the outermost thin layer having a thickness of 0.2 mm to 0.3 mm, and includes approximately 60% of water, protein, lipid, and glucose, and has therein stratum corneum, stratum granulosum, stratum spinosum, and a basal layer.

The dermic layer 33 is formed under the epidermis layer 32 having a thickness of 0.5 mm to 2 mm, has a water content of approximately 60%, includes protein, lipid and glucose, and has therein nerves, hair roots, sebaceous glands, sudoriferous glands, hair follicles, blood veins, lymph nodes.

The hypodermis 34 is formed under the dermic layer 33 having a thickness of 1 to 3 mm, and mostly consists of subcutaneous fat including 90% or more of lipid, rest being water.

In the dermic layer 33, capillary vessels are developed, and transportation of materials in response to the blood glucose occurs quickly. Therefore, the glucose concentration in the dermic layer 33 is thought to change according to the glucose concentration (blood sugar level). Accordingly, in the blood sugar level measurement apparatus 100, the irradiation unit (light source) 105 and the light receiving unit 106 are adhered to the surface of the skin 31 at a predetermined irradiation input-output distance W. In this adhered status, the irradiation unit 105 irradiates light on the surface of the skin 31. This light then is reflected by the tissues in the skin 31, and the deflection light (back scatter light) of this reflected light toward the irradiation unit 105 and the light receiving unit 106 is detected by the light receiving unit 106.

The operation of the blood sugar level measurement apparatus 100, i.e., the concentration measurement method according to an aspect of the invention will be explained hereinafter.

The blood sugar level measurement apparatus 100, when it measures the blood sugar level, dissolves a predetermined amount of glucose (first solute component) in water (solvent) to prepare glucose solution of known concentration. From the absorption coefficient measurement of this solution, the apparent absorption coefficient ($\mu'_{ag}(\lambda)$) of glucose in this solution is calculated and stored in the memory 102.

Figure 3:
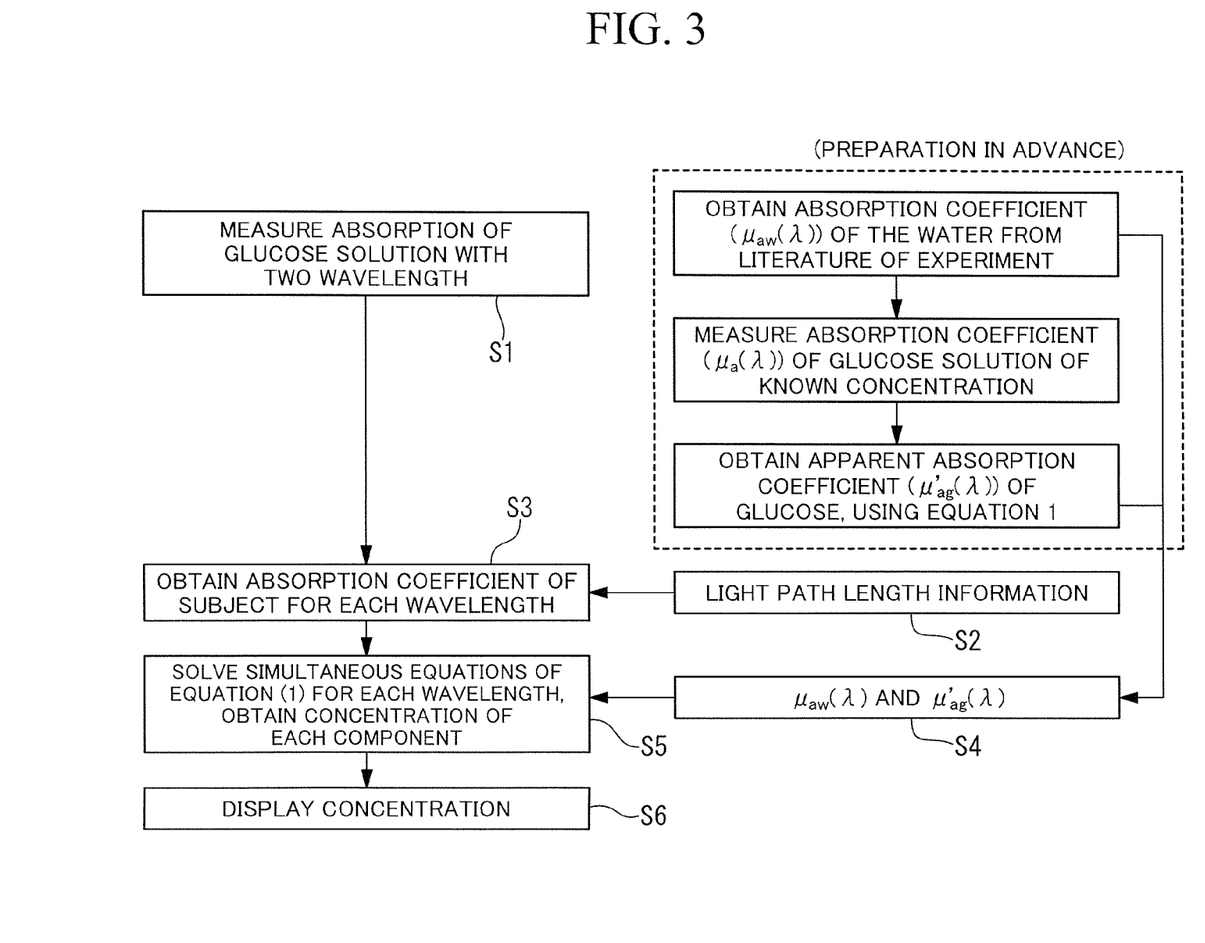
FIG. 3 is a flowchart showing the operation of the blood sugar level measurement apparatus according to the first embodiment of the invention.

FIG. 3 is a flowchart showing the operation of the blood sugar level measurement apparatus.

First, the user (measurement subject person) puts the measurement unit 107 of the blood sugar level measurement apparatus 100 at skin in the wrist or the like, and press the measurement start switch (not shown) or the like, and thereby start the operation of the blood sugar level measurement apparatus 100. The irradiation unit 105 irradiates a short-time pulse light having a wavelength $\lambda_1$ so that the apparent absorption coefficient ($\mu'_{ag}(\lambda)$) of glucose (first solute component) becomes a negative value.

The irradiation unit 105 may be constituted so that the light irradiated in the measurement have a single wavelength $\lambda_1$ or two, three, or more wavelength in sequence.

When the irradiation unit 105 irradiates light, the light receiving unit 106 receives (measures) the light irradiated from the irradiation unit 105 and back scattered by the skin 31 (S1).

Then, after the light receiving unit 106 finished receiving light, from the light path length information of the wavelength stored in the memory 102, the light path length in the skin is retrieved (S2). The calculator 101 may calculate the absorption coefficient of the skin.

The calculator 101 calculates, referring to the information (prepared in advance) stored in the memory 102, absorption coefficient ($\mu_{aw}(\lambda)$) of the water (solvent) and the apparent absorption coefficient ($\mu'_{ag}(\lambda)$) of glucose, which constitutes the body fluid (S4).

Then, for each of the light wavelength $\lambda_1$, $\lambda_2$, and so on, irradiated on the skin, based on the referenced water absorption coefficient ($\mu_{aw}(\lambda)$) and the apparent glucose absorption coefficient ($\mu'_{ag}(\lambda)$), and the absorption coefficient ($\mu_a(\lambda)$) measured by irradiating the short time pulse light attaching the measurement unit 107 on the wrist skin or the like, and by applying the following simultaneous equations (Equation 1), the volume fraction ($v_g$) of glucose (first solute component) included in the skin body fluid, and the volume fraction ($V_w$) of the solvent are obtained (S5). If the a single wavelength light was irradiated to the skin in the measurement, then Equation 1 is applied to this wavelength, and a system of Equation 1 and Equation 2 will be solved. If a plurality of lights having two or more different wavelengths were irradiated to the skin in the measurement, then Equation 1 is applied to each of those two or more wavelengths, and then the system of those two or more instances of Equation 1 may be solved.

$$\mu_a(\lambda)=\mu'_{ag}(\lambda)\cdot v_g+\mu_{aw}(\lambda)\cdot v_w \quad \text{(Equation 1)}$$

$$v_g+v_w=1 \quad \text{(Equation 2)}$$

The volume fraction ($v_g$) of glucose (first solute component) and the volume fraction ($V_w$) of the solvent thus obtained may be output to display 103, e.g., a monitor display or a printer (S6).

Hereinafter, the apparent absorption coefficient of glucose (first solute component) will be explained. The apparent absorption coefficient of glucose (first solute component) means an absorption property of solute component, including, for example, interactions with water.

Here, glucose solution of water is taken as an example to explain the apparent absorption coefficient of glucose.

Figure 7:
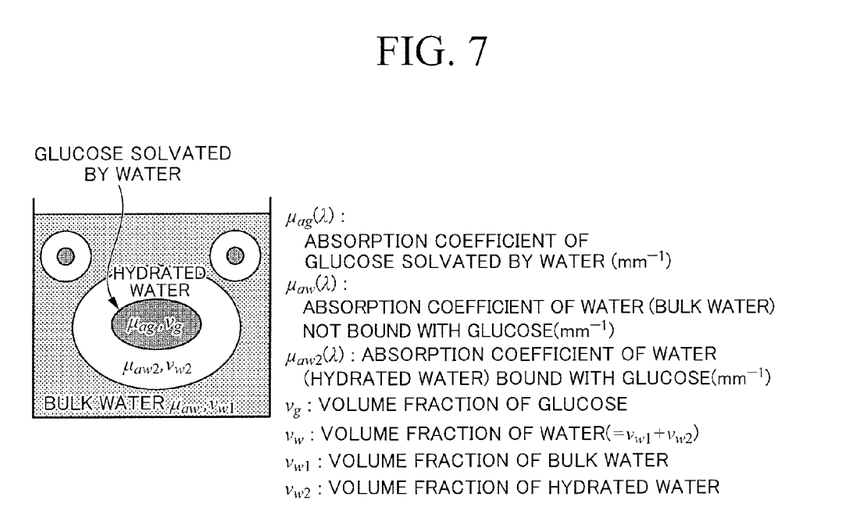
FIG. 7 is a schematic diagram showing a status of glucose solution of water.

FIG. 7 is a schematic diagram showing a status of glucose solution of water. The two components in glucose solution of water, are glucose and water. In solution of water, glucose and water is thought to incur interaction with each other via hydrogen bonds. In cases as glucose solution of water corresponding to the blood sugar level, including sufficiently large amount of water as compared to glucose, all of glucose is supposed to be under influence of hydrogen bonds, and a part of water is under such influence. Accordingly, for the water, the part bound to glucose (hydrated water) and the part not bound to glucose (bulk water) are considered as distinct components. Based on this concept, the absorption coefficient of the glucose solution of water can be given by the Equation 5.

$$\mu_a(\lambda)=\mu_{ag}(\lambda)v_g+\mu_{aw1}(\lambda)v_{w1}+\mu_{aw2}(\lambda)v_{w2} \quad \text{(Equation 5)}$$

The number of hydrogen bonds is considered to be dependent to the amount of glucose. When the sum of $v_{w1}$ and $v_{w2}$ is shown by $v_w$, using the factor of proportionality $\alpha$, Equation 5 can be translated as Equation 6.

$$\begin{aligned}\mu_a(\lambda) &= \mu_{ag}(\lambda)v_g + \mu_{aw}(\lambda)(v_w - v_{w2}) + \mu_{aw2}(\lambda)v_{w2} \quad \text{(Equation 6)}\\ &= \mu_{ag}(\lambda)v_g + \mu_{aw}(\lambda)(v_w - \alpha v_g) + \mu_{aw2}(\lambda)\alpha v_g\\ &= [\mu_{ag}(\lambda) + \alpha\{\mu_{aw2}(\lambda) - \mu_{aw}(\lambda)\}]v_g + \mu_{aw}(\lambda)v_w\\ &= \mu'_{ag}(\lambda)v_g + \mu_{aw}(\lambda)v_w\end{aligned}$$

Here, in the Equation 6, equating the content of the parenthesis [ ] by $\mu'_{ag}(\lambda)$, the apparent Beer-Lambert law is obtained. This $\mu'_{ag}(\lambda)$ is an apparent absorption coefficient, which represents the sum of "absorption coefficient $\mu_{ag}(\lambda)$ of glucose dissolved in water" and "change amount of absorption coefficient of water $\mu_{aw2}(\lambda)-\mu_{aw}(\lambda)$ times the factor of proportionality $\alpha$". In the range in which $\mu'_{ag}(\lambda)v_g$ is linear to $v_g$, i.e., in the range in which $\mu'_{ag}(\lambda)v_g$ does not change according to $v_g$, the component volume fraction can be obtained by Equation 6, treating $\mu'_{ag}(\lambda)$ as one of the physical properties.

Figure 8:
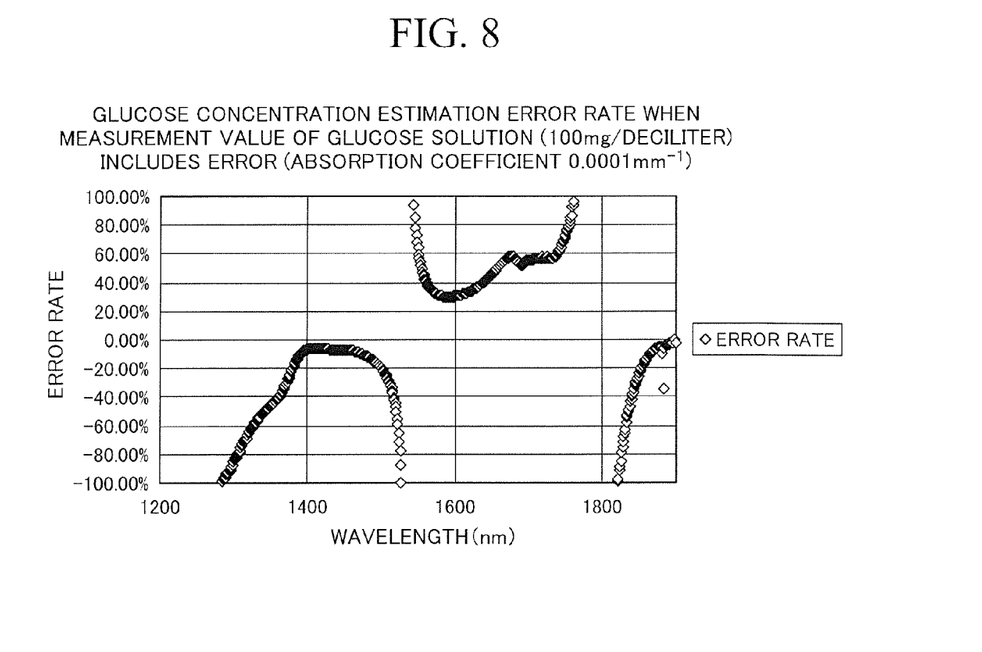
FIG. 8 is a graph showing the estimated error rate of the glucose concentration.
Figure 9:
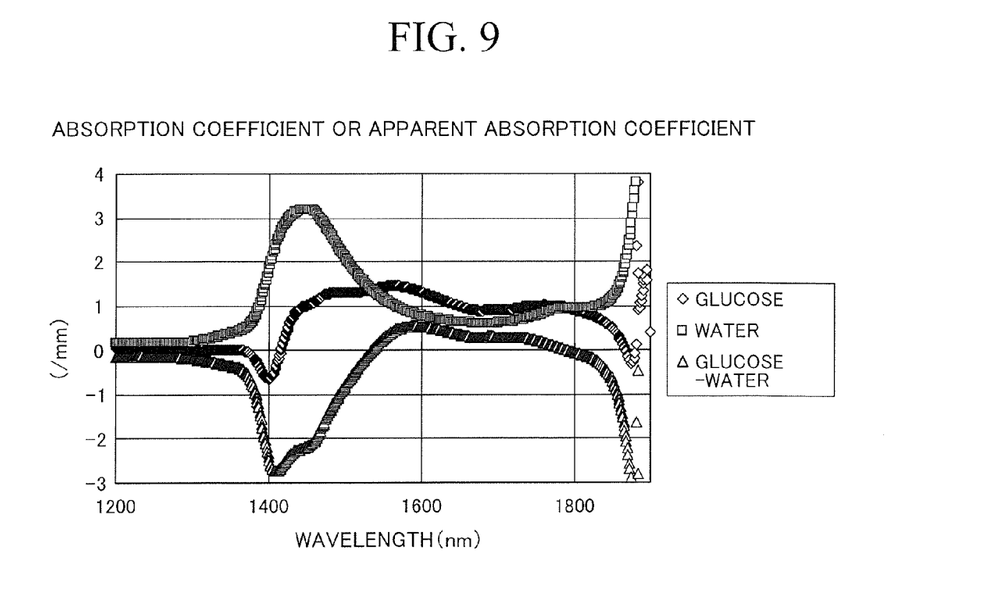
FIG. 9 is a graph showing the absorption coefficient of water, absorption coefficient of the glucose with the absorption coefficient of water subtracted, and the apparent absorption coefficient of the glucose.

In order to measure concentration of glucose solution of water, it is necessary to measure the absorption coefficient of glucose solution. When this measurement of absorption coefficient includes errors, FIG. 8 shows concentration quantitation error rates versus wavelength. Here, the measurement error was assumed to be 0.0001/mm in absorption coefficient, and Equation 7 was used for the concentration calculation.

$$\begin{cases}\mu_a(\lambda) = \mu'_{ag}(\lambda)v_g + \mu_{aw}(\lambda)v_w\\ v_g + v_w = 1\end{cases} \quad \text{(Equation 7)}$$

therefore $$v_g = \frac{\mu_a(\lambda) - \mu_{aw}(\lambda)}{\mu'_{ag}(\lambda) - \mu_{aw}(\lambda)}$$

$\mu_a(\lambda)$: absorption coefficient of glucose solution in water
$\mu_{aw}(\lambda)$: absorption coefficient of water
$\mu'_{ag}(\lambda)$: apparent absorption coefficient of glucose
$v_w$: volume fraction of water
$v_g$: volume fraction of glucose In solving simultaneous equations as the Equation 7 described above, the solution becomes less likely to be indeterminate and receive less influence from errors when the absorption coefficients of the components are distant. That is, the error rate shown in FIG. 8 becomes smaller when the absolute value of the difference between the apparent absorption coefficient of glucose and the absorption coefficient of water is larger. In the range where the apparent absorption coefficient becomes negative (wherein the inter-component interaction is large), the difference of absorption coefficients tends to be large, and the error rates are generally tend to be low. Accordingly, using the range in which the absolute value of the difference between apparent absorption coefficient of glucose and the absorption coefficient of water is large, the error rate can be further reduced.

As shown above, the embodiment of the invention refers to the information of the absorption coefficient ($\mu_{aw}(\lambda)$) of water (solvent) measured or obtained from other sources in advance and the apparent absorption coefficient of glucose ($\mu'_{ag}(\lambda)$), and calculates the volume fraction ($v_g$) of glucose (first solute component) and the volume fraction ($V_w$) of the solvent from these information and the measured absorption coefficient ($\mu_a(\lambda)$) of the sample material (body fluid in skin) in which the component concentration is unknown. Thereby, even for solutions (measurement subject) such as glucose (first solute component) dissolved in water (solvent), which contain solvent and first solute component that cause mutual interactions by dissolving or the like, the volume fraction ($v_g$) of glucose (first solute component) can be accurately measured.

Figure 10:
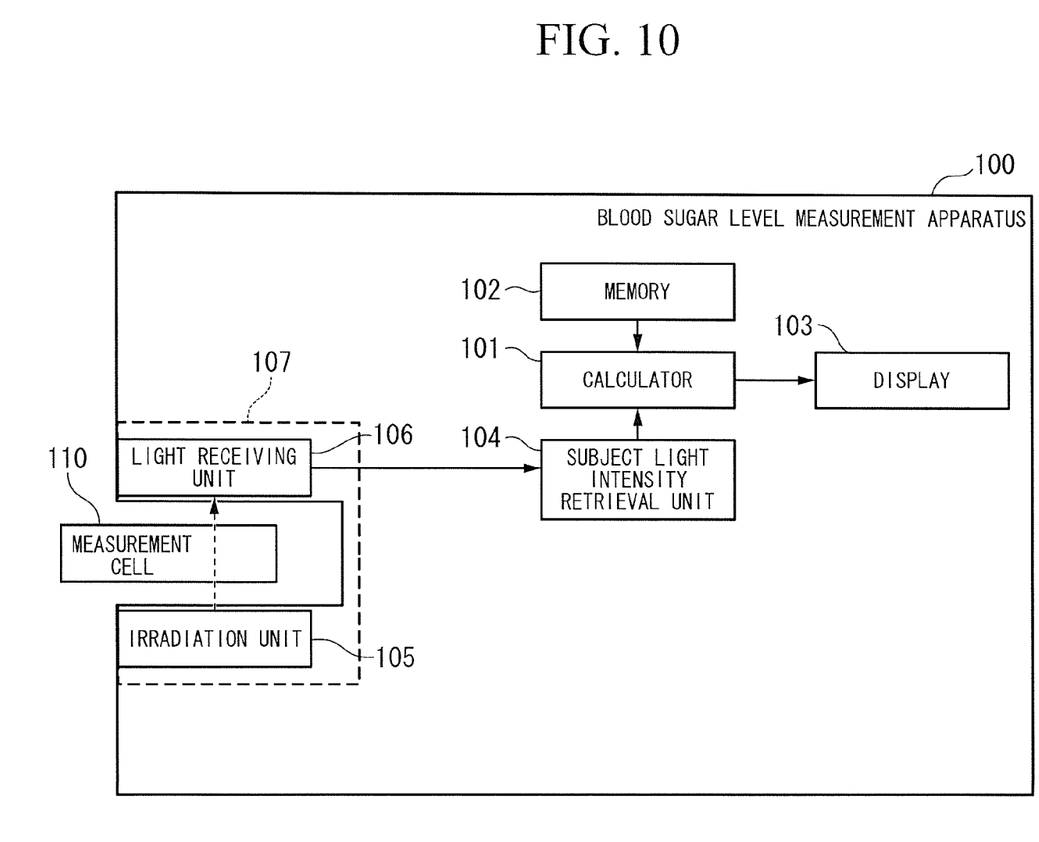
FIG. 10 is a schematic block diagram showing a modified example of the first embodiment of the present invention.

As a modified example of the first embodiment shown in FIG. 1, another constitution shown in FIG. 10 may be adopted.

In the blood sugar level measurement apparatus 100 shown in FIG. 10, body fluid or the like is sampled and injected into a glass cell 100. The glass cell 100 is placed between the irradiation unit 105 and the light receiving unit 106, in order to measure the volume fraction ($v_g$) of glucose (first solute component).

Second Embodiment

A second embodiment of the invention will be explained hereinafter. Basic configurations and methods are similar to the first embodiment. The features specific to this embodiment will be explained below.

Figure 4:
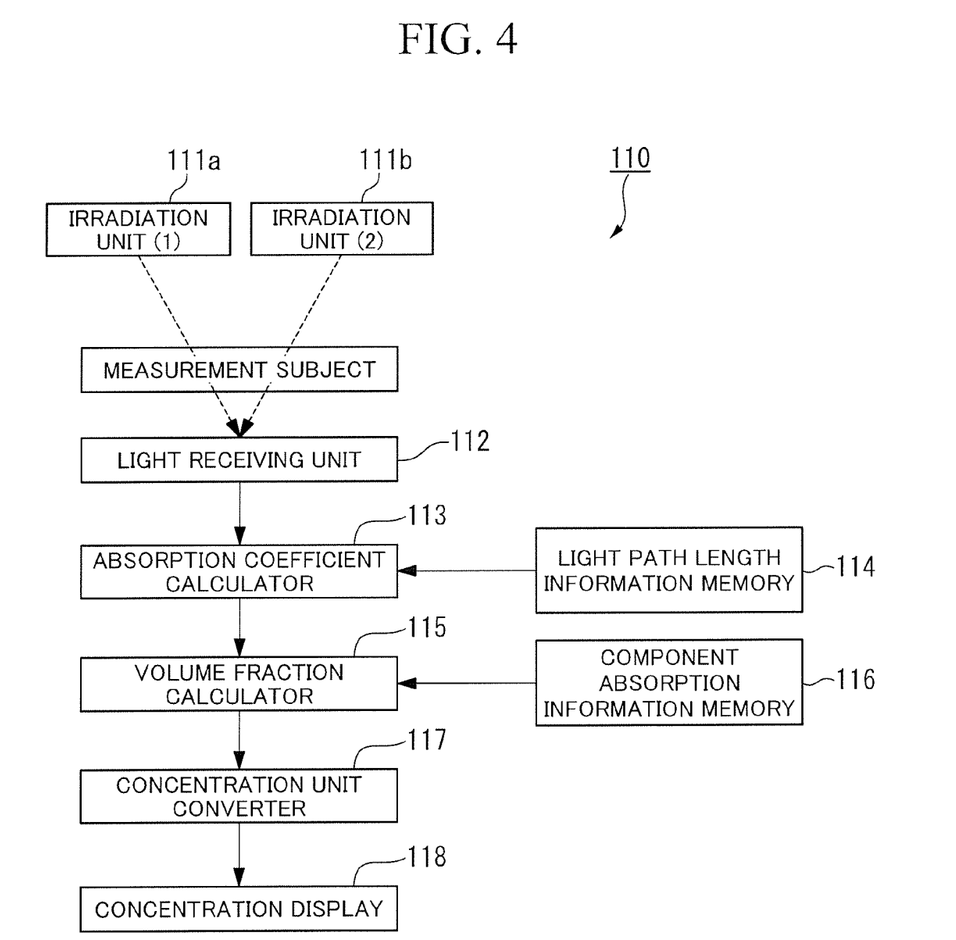
FIG. 4 is a flowchart showing the operation of the blood sugar level measurement apparatus according to a second embodiment of the invention, measuring a blood sugar level.

FIG. 4 shows the constitution and the flow of the blood sugar level measurement in a blood sugar level measurement apparatus according to the second embodiment.

The blood sugar level measurement apparatus 110 includes two irradiation units (light source) 111a and 111b which outputs light having two different wavelengths. From this irradiation units (light source) 111a and 111b toward the measurement subject, e.g., skin, two distinctive light having distinct wavelength is irradiated The light is, for example, short time pulse light having a wavelength which cause the apparent absorption coefficient of glucose (first solute component) ($\mu'_{ag}(\lambda)$) to be a negative value.

Then the light receiving unit 112 receives light from each of the irradiation units (light source) 111a and 111b back scattered by the skin (measurement subject). Thereafter, the absorption coefficient calculator 113 retrieves light path length information corresponding to wavelength $\lambda_1$ from the light path length information memory 114, and calculates absorption coefficient ($\mu_a(\lambda)$) included in the body fluid contained in the skin.

Then, the volume fraction calculator 115 refers to the component absorption information memory (memory) 116 and retrieves information of absorption coefficient ($\mu_{aw}(\lambda)$) of water (solvent) and apparent absorption coefficient of glucose ($\mu'_{ag}(\lambda)$), which is measured in advance, or obtained from other sources. Then, from the information of component absorption information memory (memory) 116 and measured absorption coefficient ($\mu_a(\lambda)$) of the sample material in which the glucose concentration is unknown (body fluid in skin), the volume fractions of glucose (first solute component) and water (solvent) are calculated. Then, the concentration unit converter 117 converts the units of the volume fractions of glucose (first solute component) and the water (solvent) into molar concentrations. Thus obtained molar concentration ($C_g$) of glucose (first solute component) and the molar concentration ($C_w$) of water (solvent) are displayed in the concentration display 118.

Third Embodiment

A third embodiment of the invention is explained hereinafter. Basic configurations and methods are similar to the first embodiment. The features specific to this embodiment will be explained below.

Figure 5:
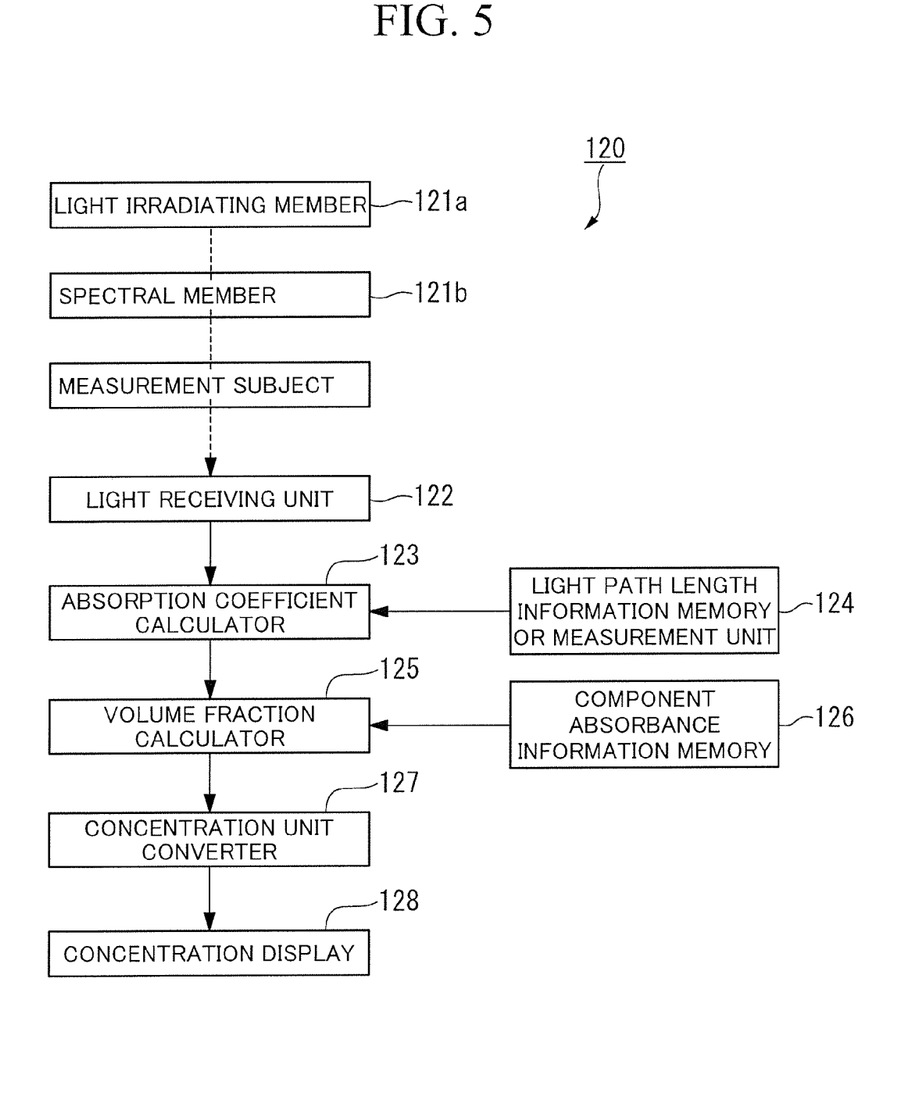
FIG. 5 is a schematic block diagram showing a blood sugar level measurement apparatus according to the third embodiment.

FIG. 5 shows the constitution and the measurement flow of a blood sugar level measurement apparatus according to the third embodiment.

The blood sugar level measurement apparatus 120 of this embodiment includes a light irradiating member (light source) 121a which irradiates light including a plurality of wavelengths, e.g., white light, and a spectral member 121b that separates the light irradiated from the irradiating member (light source) 121a into a plurality of light each having distinct wavelength. The plurality of light each having distinct wavelength is irradiated toward the measurement subject, e.g., skin.

The light receiving unit 122 receives the back scattered light by the skin (measurement subject) from the light separated by the spectral member 121b having the plurality of wavelengths. Then the absorption coefficient calculator 123 referrers to the light path length information memory 124, and calculates the absorption coefficient ($\mu_a(\lambda)$) of the body fluid included in the skin, from the light path length of wavelength $\lambda_1$.

Then the volume fraction calculator 125 referrers to the information of an absorption coefficient ($\mu_{aw}(\lambda)$) of water (solvent) measured or obtained from other source in advance and an apparent absorption coefficient of glucose ($\mu'_{ag}(\lambda)$). Then, from the information in component absorbance information memory (memory) 126 and the measured absorption coefficient ($\mu_a(\lambda)$) of sample material (body fluid in skin) in which the glucose concentration is unknown, the volume fractions of glucose (first solute component) and water (solvent). Then, in the concentration unit converter 127, the volume fractions of glucose (first solute component) and water (solvent) are converted into the units of molar concentration. Thus obtained molar concentration ($C_g$) of glucose (first solute component) and the molar concentration ($C_w$) of water (solvent) are displayed in the concentration display 128.

Forth Embodiment

A fourth embodiment of the invention is explained hereinafter. Basic configurations and methods are similar to the first embodiment. The features specific to this embodiment will be explained below.

The apparatus in the aforementioned embodiments may further measure (quantitate) the second solute component included in the body fluid in skin as the sample material as the measurement subject. For example, in addition to glucose (first solute component) included in the body fluid, which interacts with water (solvent), salts (e.g., NaCl) which interacts with water (solvent) may also be measured.

In such measurement of the second solute component, the memory of the blood sugar level measurement apparatus stores in advance the absorption coefficient ($\mu_{aw}(\lambda)$) of water (solvent), the apparent absorption coefficient of glucose ($\mu'_{ag}(\lambda)$) after the interaction between water (solvent) and glucose (first solute component) has occurred, and the apparent absorption coefficient ($\mu'_{an}(\lambda)$) of NaCl.

Figure 6:
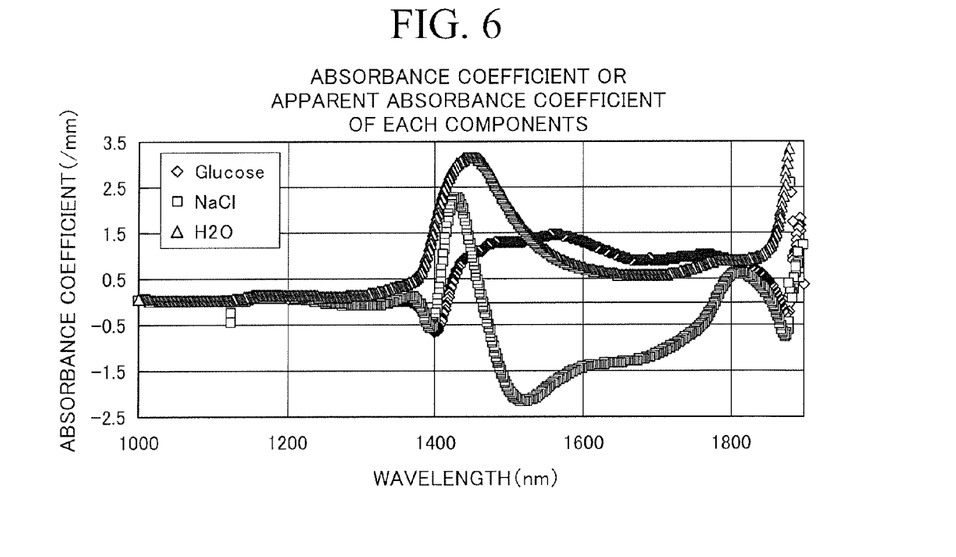
FIG. 6 is a graph showing an absorption coefficient, and an apparent absorption coefficient of a component including NaCl.

Then the absorption coefficient ($\mu_a(\lambda)$) of the second sample material in which the glucose and NaCl concentrations are unknown (e.g., body fluid in skin), is measured after the interaction between the water and glucose, and the interaction between water and NaCl have occurred. In the measurement, the irradiation unit 105 irradiates, for example, a light which has a wavelength which causes the apparent absorption coefficient ($\mu'_{ag}(\lambda)$) of glucose to be a negative values, and a light which causes an apparent absorption coefficient ($\mu'_{an}(\lambda)$) of NaCl to be a negative value, toward the skin. Then the back scatter light of the irradiated light is received with the light receiving member. FIG. 6 shows the change of absorption coefficient of water, and the apparent absorption coefficient of glucose and water, according to the wavelength.

Then, the absorption coefficient ($\mu_{aw}(\lambda)$) of water (solvent), the apparent absorption coefficient of glucose ($\mu'_{ag}(\lambda)$) after the interaction between water (solvent) and glucose (first solute component), the apparent absorption coefficient ($\mu'_{an}(\lambda)$) of the NaCl after the interaction between the water (solvent) and the NaCl (second solute component), and the measured absorption coefficient ($\mu_a(\lambda)$) of the sample material (skin) are applied to the simultaneous equations (Equations 3 and 4). As a result, the volume fractions ($v_g$), ($V_n$), ($V_w$) of glucose (first solute component), NaCl (second solute component), and water (solvent) are obtained. Then, the concentration unit converter converts the volume fractions of glucose (first solute component), NaCl (second solute component) and water (solvent) into the units of molar concentration. Thus obtained molar concentrations ($C_g$), ($C_a$), ($C_w$) of glucose (first solute component), NaCl (second solute component), the water (solvent) are displayed in the display. If lights with two different wavelengths were irradiated to the skin in the measurement, then Equation 3 is applied to each of those two wavelengths, and a system containing those two instances of Equation 3 and Equation 4 will be solved. If a plurality of lights having a two or more different wavelengths were irradiated to the skin in the measurement, then Equation 3 is applied to each of those two or more wavelengths, and then the system of two or more instances of Equation 3 may be solved. The number of wavelengths irradiated to the skin is preferably equal to or more than the number of the subject components to be measured in the sample material.)

$$\mu_a(\lambda)=\mu'_{ag}(\lambda)\cdot v_g+\mu'_{an}(\lambda)\cdot v_n+\mu_{aw}\cdot v_w \qquad \text{(Equation 3)}$$

$$v_g+v_n+v_w=1 \qquad \text{(Equation 4)}$$

According to the above-explained embodiment, from a sample material including a plurality of solute components (first solute component, second solute component) which interact with the solvent, accurate concentrations of the first solute component and the second solute component can be reliably obtained by an easy and non-invasive manner.

While embodiments of the invention have been described and illustrated above, these are exemplary of the invention and are not to be considered as limiting. Additions, omissions, substitutions, and other modifications can be made without departing from the scope of the invention.

For example, in the above-explained embodiments, blood sugar level measurement apparatus is used as the concentration measurement apparatus, and human palm skin is used as the observation target, and glucose, NaCl as the target component. Thereby, in the exemplary case, concentrations of glucose, NaCl was measured. However, the invention is not limited to this example. Any concentration measurement apparatus, concentration measurement method which quantitates each concentration of any components in which the components mutually interact with any solvent.

The Equations (Equations 1, 2, 3, and 4) used to obtain the component volume fractions represent the relationship of "absorption coefficient is equal to absorption coefficient times volume fraction". However, each of the equations (Equations 8, and 9) representing the relationship of "absorption coefficient is equal to molar absorption coefficient times molar concentration" may also be used. In this case, the molar concentrations will be directly obtained, instead of the volume fractions.

Furthermore, although the molar concentration was displayed in the embodiments, not limited by those cases, the unit converter may convert the unit to, for example, mg/deciliter, in which the concentration is represented by weight per volume, and the values may be displayed in the concentration display.

$$\mu_a(\lambda)=\epsilon'_g(\lambda)C_g+\epsilon_w(\lambda)C_w \qquad \text{(Equation 8)}$$

$$\mu_a(\lambda)=\epsilon'_g(\lambda)C_g+\epsilon'_n(\lambda)C_n+\epsilon_w(\lambda)C_w \qquad \text{(Equation 9)}$$

$\mu_a(\lambda)$: absorption coefficient of measurement subject (solution in water)
$\epsilon'_g(\lambda)$: apparent molar absorption coefficient of glucose
$\epsilon'_n(\lambda)$: apparent molar absorption coefficient of NaCl
$\epsilon'_w(\lambda)$: apparent absorption coefficient of water
$C_g$: molar concentration of glucose
$C_n$: molar concentration of NaCl
$C_w$: molar concentration of water

What is claimed is:

1. A concentration measurement method by an absorptiometric method which measures a concentration of a first solute component dissolved in a solution, in which the first solute component interacts with a solvent, comprising:
    referring to an absorption coefficient ($\mu_{aw}(\lambda)$) of the solvent;
    referring to an apparent absorption coefficient ($\mu'_{ag}(\lambda)$) of the first solute component, which is measured in advance, after an interaction between the solvent and the first solute component has occurred;
    measuring an absorption coefficient ($\mu_a(\lambda)$) of a first sample material, after the interaction between the solvent and the first solute component has occurred; and
    obtaining an unknown volume fraction ($v_g$) of the first solute component and a volume fraction ($v_w$) of the solvent, based on the absorption coefficient ($\mu_{aw}(\lambda)$) of the solvent, the apparent absorption coefficient ($\mu'_{ag}(\lambda)$) of the first solute component, and the absorption coefficient ($\mu_a(\lambda)$) of the first sample material, by solving a system of instances of Equation 1 applied to two different wavelengths, or by solving a system of Equation 1 applied to one wavelength and Equation 2

$$\mu_a(\lambda)=\mu'_{ag}(\lambda)\cdot v_g+\mu_{aw}(\lambda)\cdot v_w \qquad \text{(Equation 1)}$$

$$v_g+v_w=1 \qquad \text{(Equation 2)}.$$

2. The concentration measurement method according to claim 1, wherein
    in the measuring the absorption coefficient ($\mu_a(\lambda)$) of the first sample material, a light source wavelength of the absorptiometric method is set so that the apparent absorption coefficient ($\mu'_{ag}(\lambda)$) of the first solute component or the apparent absorption coefficient ($\mu'_{an}(\lambda)$) of the second solute component becomes a negative value.

3. The concentration measurement method according to claim 2, wherein the light source wavelength is in the range of 1370 nm to 1510 nm, or in the range of 1550 nm to 1740 nm.

4. The concentration measurement method according to claim 2, wherein the light source wavelength is in the range of 1370 nm to 1420 nm.

5. A concentration measurement method by an absorptiometric method which measures a concentration of a solute component dissolved in a solution, in which the solute component interacts with a solvent, comprising:
referring to an absorption coefficient ($\mu_{aw}(\lambda)$) of the solvent;
referring to an apparent absorption coefficient ($\mu'_{ag}(\lambda)$) of a first solute component, which is measured in advance, after an interaction between the solvent and the first solute component has occurred;
referring to an apparent absorption coefficient ($\mu'_{an}(\lambda)$) of a second solute component, which is measured in advance, after an interaction between the solvent and the second solute component has occurred;
measuring an absorption coefficient ($\mu_a(\lambda)$) of a first sample material, after the interaction between the solvent and the first solute component and the interaction between the solvent and the second solute component have occurred; and
obtaining a volume fraction ($v_g$) of the first solute component, a volume fraction ($v_n$) of the second solute component, and a volume fraction ($v_w$) of the solvent, based on the absorption coefficient ($\mu_{aw}(\lambda)$) of the solvent, the apparent absorption coefficient ($\mu'_{ag}(\lambda)$) of the first solute component, the apparent absorption coefficient ($\mu'_{an}(\lambda)$) of the second solute component, and the absorption coefficient ($\mu_a(\lambda)$) of the first sample material, by solving a system of instances of Equation 3 applied to three different wavelengths, or by solving a system of instances of Equation 3 applied to two different wavelengths and Equation 4

$$\mu_a(\lambda)=\mu'_{ag}(\lambda)\cdot v_g+\mu'_{an}(\lambda)\cdot v_n+\mu_{aw}\cdot v_w \quad \text{(Equation 3)}$$

$$v_g+v_w=1 \quad \text{(Equation 4)}.$$

6. The concentration measurement method according to claim 5, wherein
in the measuring the absorption coefficient ($\mu_a(\lambda)$) of the first sample material, a light source wavelength of the absorptiometric method is set so that the apparent absorption coefficient ($\mu'_{ag}(\lambda)$) of the first solute component or the apparent absorption coefficient ($\mu'_{an}(\lambda)$) of the second solute component becomes a negative value.

7. The concentration measurement method according to claim 6, wherein the light source wavelength is in the range of 1370 nm to 1510 nm, or in the range of 1550 nm to 1740 nm.

8. The concentration measurement method according to claim 6, wherein the light source wavelength is in the range of 1370 nm to 1420 nm.

9. A concentration measurement apparatus that measures a concentration of a first solute component in a solution, in which the first solute component interacts with a solvent, the concentration measurement apparatus comprising:
a memory that stores an absorption coefficient ($\mu_{aw}(\lambda)$) of the solvent, an apparent absorption coefficient ($\mu'_{ag}(\lambda)$) of the first solute component measured in advance after an interaction occurred between the solvent and the first solute component;
a measurement part that measures an absorption coefficient ($\mu_a(\lambda)$) of a first sample material in which a concentration of the first solute component is unknown, after the interaction between the solvent and the first solute component has occurred;
a light source that irradiates a light of a predetermined wavelength at the first sample material; and
a calculator that calculates a volume fraction ($v_g$) of the first solute component and a volume fraction of the solvent ($v_w$), based on the absorption coefficient ($\mu_{aw}(\lambda)$) of the solvent, the apparent absorption coefficient ($\mu'_{ag}(\lambda)$) of the first solute component, and the absorption coefficient ($\mu_a(\lambda)$) of the first sample material, by solving a system of instances of Equation 1 applied to two different wavelengths, or by solving a system of Equation 1 applied to one wavelength and Equation 2

$$\mu_a(\lambda)=\mu'_{ag}(\lambda)\cdot v_g+\mu_{aw}(\lambda)\cdot v_w \quad \text{(Equation 1)}$$

$$v_g+v_w=1 \quad \text{(Equation 2)}.$$

10. The concentration measurement apparatus according to claim 9, wherein the light source irradiates a light having a wavelength so that the apparent absorption coefficient ($\mu'_{ag}(\lambda)$) of the first solute component or the apparent absorption coefficient ($\mu'_{an}(\lambda)$) of the second solute component becomes a negative value.

11. A concentration measurement apparatus that measures a concentration of a first solute component in a solution, in which the first solute component interacts with a solvent, the concentration measurement apparatus comprising:
a memory that stores an absorption coefficient ($\mu_{aw}(\lambda)$) of the solvent, an apparent absorption coefficient ($\mu'_{ag}(\lambda)$) of the first solute component measured in advance after an interaction occurred between the solvent and the first solute component, and an apparent absorption coefficient ($\mu'_{an}(\lambda)$) of the second solute component measured in advance after an interaction occurred between the solvent and the second solute component;
a measurement part that measures an absorption coefficient ($\mu_a(\lambda)$) of a first sample material in which a concentration of the first solute component and a concentration of the second solute component, after the interaction between the solvent and the first solute component and the interaction between the solvent and the second solute component have occurred, are unknown;
a light source that irradiates a light of a predetermined wavelength at the first sample material; and
a calculator that calculates a volume fraction ($v_n$) of the second solute component, and a volume fraction of the solvent ($v_w$), based on the absorption coefficient ($\mu_{aw}(\lambda)$) of the solvent, the apparent absorption coefficient ($\mu'_{ag}(\lambda)$) of the first solute component, the apparent absorption coefficient ($\mu'_{an}(\lambda)$) of the second solute component, and the absorption coefficient ($\mu_a(\lambda)$) of the first sample material, by solving a system of instances of Equation 3 applied to three different wavelengths, or by solving a system of instances of Equation 3 applied to two different wavelengths and Equation 4.

$$\mu_a(\lambda)=\mu'_{ag}(\lambda)\cdot v_g+\mu'_{an}(\lambda)\cdot v_n+\mu_{aw}\cdot v_w \quad \text{(Equation 3)}$$

$$v_g+v_n+v_w=1 \quad \text{(Equation 4)}.$$

12. The concentration measurement apparatus according to claim 11, wherein the light source irradiates a light having a wavelength so that the apparent absorption coefficient ($\mu'_{ag}$ ($\lambda$)) of the first solute component or the apparent absorption coefficient ($\mu'_{an}(\lambda)$) of the second solute component becomes a negative value.

* * * * *